United States Patent [19]

Graham

[11] 4,150,108
[45] Apr. 17, 1979

[54] INJECTABLE MEDICINAL COMPOSITIONS

[76] Inventor: Neil B. Graham, 6, Kilmardinny Grove, Bearsden, Glasgow, Scotland

[21] Appl. No.: 892,911

[22] Filed: Apr. 3, 1978

Related U.S. Application Data

[63] Continuation-in-part of Ser. No. 751,955, Dec. 17, 1976, abandoned.

[30] Foreign Application Priority Data

Dec. 29, 1975 [GB] United Kingdom ............... 52935/75

[51] Int. Cl.² .................. A61K 31/74; A61K 31/765; A61K 9/26; A61K 47/00
[52] U.S. Cl. ......................................... 424/22; 424/19
[58] Field of Search ................................... 424/19–22, 424/78

[56] References Cited

U.S. PATENT DOCUMENTS

| | | | |
|---|---|---|---|
| 3,978,203 | 8/1976 | Wise | 424/22 |
| 4,093,709 | 6/1978 | Chol et al. | 424/19 |

*Primary Examiner*—Shep K. Rose

*Attorney, Agent, or Firm*—Brady, O'Boyle & Gates

[57] ABSTRACT

A medicinal composition comprising a steroid compound entrapped within a polymeric matrix composed of a copolymer of a compound containing two or more groups selected from the group consisting of OH and —COOH groups and a bisdihydropyron of the general

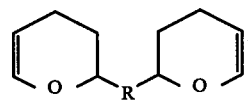

(I)

wherein R is an organic bridging group which is unreactive to the OH or —COOH groups.

The most preferred bridging group is one which contains one or more ester groups. Any bridge which is non-reactive to the comonomer containing the —OH or —COOH groups can be used. Another preferred compound is the product of the added condensation of 2-formyl-3, 4-dihydro-2H-pyron.

7 Claims, No Drawings

INJECTABLE MEDICINAL COMPOSITIONS

This application is a Continuation-In-Part of copending application Ser. No. 751,955, filed Dec. 17, 1976, now abandoned.

The present invention relates to medicinal compositions. More particularly, the invention is concerned with medicinal compositions comprising in admixture a steroid and polymeric carrier, the carrier gradually releasing the steroid on administration of the medicinal composition to the body. The invention is also concerned with a process for the preparation of said medicinal compositions.

Polymers used as carriers in delayed-release medicinal compositions which are to be administered repeatedly for prolonged periods may give rise to problems if the body cannot readily metabolise them without the formation of harmful products. In general, such compositions have not used polymers as carriers since those polymers which are readily available have been developed primarily for their stability in nonmedical applications and are not readily metabolised.

According to the present invention there is provided a medicinal composition comprising a steroid compound entrapped within a polymeric matrix composed of a copolymer of a compound containing two or more groups selected from the group consisting of OH and —COOH groups and a bisdihydropyran of general formula I

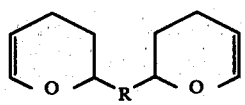
(I)

wherein R is an organic bridging group which is unreactive to the OH or —COOH groups.

The most preferred bridging group is one which contains one or more ester groups. Thus, preferred compounds of formula I are:

II

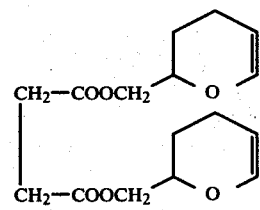
III

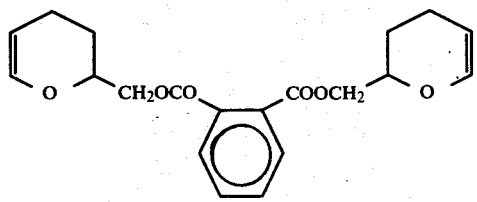
IV

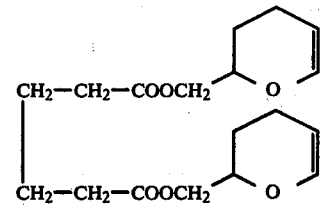
V

However, it is possible to utilise any bridge which is non-reactive to the comonomer containing the —OH or —COOH groups, for example a hydrocarbon bridge can be used.

Another preferred compound of general formula I is the product of the aldol condensation of 2-formyl-3,4-dihydro-2H-pyran, which product is believed to have the molecular structural formula VI

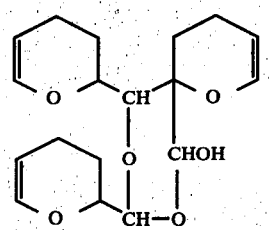
VI

The polymers containing these dihydropyranyl groups are readily hydrolysed by body fluids thereby releasing the entrapped steroid over a period of time. It has been found, in general terms, that as the number of aliphatic ester groups in the bridge R is increased the ease with which the compound I can be hydrolysed increases, whereas the use of aromatic ester groups in R, such as in compound IV, increases the resistance of the polymer to hydrolysis. It is thus possible to utilise these opposing effects to produce matrices which are hydrolysed at a preselected rate and thus design compositions in which the rate of release of the steroid corresponds to a pharmacologically indicated dosage rate.

In a preferred embodiment of this invention, the copolymer is cross-linked and forms a matrix which holds the steroidal material.

The compound having two or more groups selected from OH and COOH groups is preferably a compound which occurs naturally in and/or is benign to the human body. Examples of compounds containing two or more groups selected from OH and COOH groups which can be used in the present invention are:

a. among the compounds having two or more OH groups, glycerol, sorbitol, erythritol, inositol, glycols based on polyethylene oxide, 4,4'-dihydroxyphenyl-2,2-propane, 1,2-dihydroxy-benzene, 1,3-dihydroxy-benzene, 1,4-dihydroxy-benzene, 1,2,3-trihydroxy-benzene, 1,2,4-trihydroxy-benzene, 1,3,5-trihydroxy-benzene and the like;

b. among the compounds having at least one OH group and at least one COOH group, lactic acid, malic acid, 2-hydroxy-isobutyric acid, 10-hydroxydecanoic acid, 12-hydroxyoctadecanoic acid, 12-hydroxy-(cis)-9-octadecenoic acid, 2-hydroxycyclo-hexanecarboxylic acid (hexahydrosalicyclic acid), 2-hydroxy-2-phenyl-(D)-propionic acid, diphenylhydroxyacetic acid, ascorbic acid, citric acid, tartaric acid, 2-hydroxy-3-methyl-(D)-succinic acid, 2-hydroxybenzoic acid, 3-hydroxybenzoic acid, 4-hydroxybenzoic acid, 2,3-dihydroxybenzoic acid, 2,4-dihydroxybenzoic acid, 2,5-dihydroxybenzoic acid, 2,6-dihydroxybenzoic acid, 2,3,4-trihydroxybenzoic acid, 2,4,5-trihydroxybenzoic acid, 2,4,6-trihydroxybenzoic acid, 3,4,5-trihydroxybenzoic acid and the like;

c. among the compounds having two or more COOH groups, oxalic acid, malonic acid, succinic acid, glutaric acid, adipic acid, 1,2-cyclohexanedicarboxylic acid, 1,3-cyclohexanedicarboxylic acid, 1,4-cyclohexanedicarboxylic acid, phthalic acid, isophthalic acid, teraphthalic acid and the like.

A mixture of such compounds can also be used.

The steroidal material which is present in the medicinal compositions provided by this invention can be one or more steroids for which a controlled release is desired. For example, the steroid can be norethisterone, norethisterone acetate, spironolactone, cortisone, etc. In a preferred embodiment of this invention the steroid is norethisterone or norethisterone acetate.

The ratio of steroid to copolymer which can be present in the medicinal compositions of this invention can vary within wide limits. Preferably the weight of steroid is at least about equal to the weight of copolymer, and it may be possible to have a steroid to copolymer weight ratio of up to 90:10. A steroid to copolymer ratio of from about 50:50 by weight to about 60:40 by weight is particularly suitable.

According to the process provided by the present invention, the medicinal compositions of this invention are prepared by copolymerising a compound of formula I hereinbefore with at least one compound having more than one group selected from OH and COOH groups in the presence of acidic catalyst and in the presence of steroidal material.

The compound of formula I hereinbefore, which is a mixture of stereoisomers, is a colourless liquid having a high boiling point, a very low level of oral toxicity and no known detrimetal effect on skin. It may be prepared according to the following reaction sequence:

$H_2C=CH-CH_3$     Propylene

↓ $O_2$ $H_2C=CH-CHO$     Acrolein

↓ Heat to 190° C

Acrolein dimer

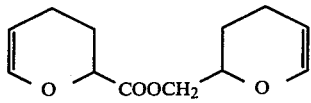

↓ Metal alkoxide

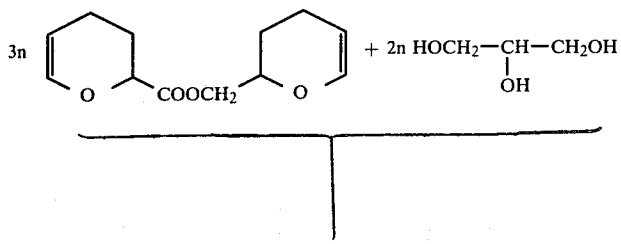

(I)

The process provided by the present invention may be carried out by simply mixing the compound of formula I with a compound having two or more groups selected from OH and COOH groups or with a mixture of such compounds in the presence of an acidic catalyst, advantageously at an elevated temperature such as from about 60° C. to 100° C., especially at about 80° C., and then adding to the resulting mixture and homogeneously distributing therein the appropriate amount of the desired steroid. The mixture thus obtained can then be allowed to cure, suitably at an elevated temperature.

In certain circumstances it may be desirable to interrupt the copolymerisation during the initial mixing of the compound of formula I with a compound having two or more groups selected from OH and COOH groups or with a mixture of such compounds. This can be effected, for example, by the addition of an amount of a primary, secondary or tertiary amine such as triethylamine, a quaternary ammonium hydroxide or a basic inorganic oxide or hydroxide sufficient to neutralise the activity of the acidic catalyst. The steroid can then be added to and homogeneously distributed in the resulting mixture and subsequently the copolymerisation can be allowed to proceed to completion by the addition of further acidic catalyst.

Suitable acidic catalysts which may be used in the present process include inorganic acids such as hydrochloric acid, sulphuric acid etc, organic acids such as paratoluenesulphonic acid etc and Lewis acids such as zinc chloride, tin tetrachloride, aluminium chloride, ferric chloride etc. The preferred acidic catalyst is ferric chloride. The amount of acidic catalyst used is not critical, but it is expedient to use from about 0.01% to 2.0%, particularly from about 0.04% to about 1.0% based on the total weight of the mixture.

The ratio of compound of formula I to compound having two or more groups selected from OH and COOH groups can be varied. It is convenient to use stoichiometric amounts, although the use of amounts which deviate considerably from stoichiometry is also possible.

The copolymerization may also be carried out in the presence of an inert pharmaceutically acceptable solvent or an inert pharmaceutically acceptable oil, whereby the nature of the resulting medicinal composition is modified. An example of such an oil is olive oil. The inert pharmaceutically acceptable solvent or oil may be added as such or it may serve as a solvent or dispersant for other components of the copolymerization mixture. Thus, for example, the steroid may be dissolved or dispersed in the inert pharmaceutically acceptable solvent or oil.

The following is a simplified representation of the preparation of a cross-linked copolymer using the compound of formula II and glycerol:

$3n$ <image (structure)> $+ 2n\ HOCH_2-CH-CH_2OH$
                                                                        $OH$ -continued

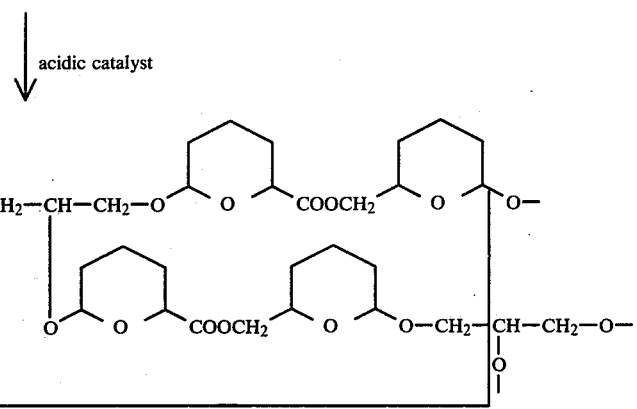

Following administration of the medicinal compositions of this invention to the body, the steroid is gradually released therefrom over a period of, for example, 3 months to 2 years and, at the same time, the copolymer is biodegraded to substances which can be readily disposed of by the body. As mentioned earlier, the copolymer is preferably one formed between the compound of formula I and a compound which occurs naturally in and/or is benign to the human body. Hydrolysis, especially acid hydrolysis, of such copolymers yields predominantly the latter compounds themselves. In the case of a copolymer prepared using glycerol as illustrated hereinbefore, the hydrolysis fragments of the compound of formula II are the following:

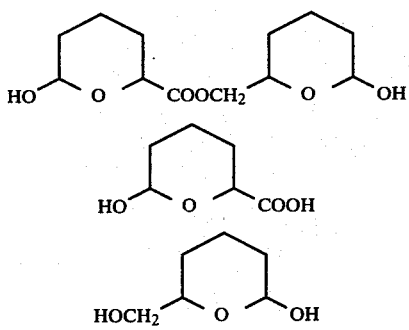

(II)

(III)

(IV)

, all of which are readily oxidisable for disposal by the body.

The rate of release of the steroid from a medicinal composition provided by this invention can be controlled by a variety of methods. For example, in a copolymer prepared using given components the density of the cross-linking can be altered. Again, for example, the nature and amount of inert pharmaceutically acceptable solvent or oil which may be present in the compositions can be varied.

A particular feature of medicinal compositions provided by the present invention which are based on cross-linked copolymers (i.e. matrices) is that such copolymers have a so-called glassy state (in which they are hard and brittle) and a rubber-like state, the change from the glassy state to the rubber-like state occurring at the so-called glass transition temperature. Following administration of such medicinal composition having the copolymer in the glassy state the steroid is gradually released and, at the same time, the copolymer is gradually biodegraded, this resulting in a gradual reduction of the glass transition temperature. When the glass transition temperature is reached the rubber-like state occurs and the copolymer becomes completely biodegraded. Thus, if the glass transition temperature reaches body temperature, there is a rapid onset in the degradation. It will accordingly be evident that it is highly desirable to provide medicinal compositions based on cross-linked copolymers which initially have a glass transition temperature which lies somewhat above body temperature.

The medicinal compositions provided by the present invention may be administered, for example, by subcutaneous or intramuscular injection or inplantation. In the case of forms for injection, a medicinal composition of appropriate particle size can be dispersed in a pharmaceutically acceptable carrier material adapted for subcutaneous or intramuscular administration. By appropriate choice of particle size and particle size distribution in the dispersant, the rate of release of the steroid can be controlled. Forms adapted for implantation include, for example, pellets, films, discs, rods and the like. Such implant forms can be prepared in a conventional manner.

The following Examples illustrate the present invention:

EXAMPLE 1

The following ingredients were used to prepare a polymer matrix having a ratio of compound I to glycerol of 3:2 and containing 50% by weight of norethisterone:

| | |
|---|---|
| Glycerol | 215.5 mg |
| 3,4-Dihydro-2H-pyran-2-methyl-(3,4--dihydro-2H-pyran-2-carboxylate) (Compound I) | 790.0 mg |
| Ferric chloride | 1.0 mg |
| Norethisterone | 1006.5 mg |

A solution of the ferric chloride in the glycerol was warmed to 80° C. and the compound I was added dropwise while warming and stirring between the additions. Compound I is initially incompatible with the glycerol, but by gradual additions and warming until the mixture becomes one phase, a stage is reached when the glycerol mixture will more readily accept the additions of compound I and become homogeneous.

After stoichiometric amounts of compound I to glycerol have been reached, the mixture is removed from the heating source and the norethisterone is added and worked-in to form a homogeneous paste. This paste is subsequently maintained at a temperature of 80° C. until polymerisation is complete and the desired polymer matrix is obtained.

The paste referred to in the preceding paragraph can be used to prepare discs for implantation as follows:

Prior to the final polymerisation stae, the paste is spread on a film of Polythene, covered with a second film of Polythene and placed in a press which, when closed, leaves a gap between the Polythene films of the desired thickness for the copolymer matrix. A temperature of 80° C. is applied to the paste until polymerisation is complete. The film of norethisterone/polymer matrix is punched while still soft to produce flat discs and, after hardening has taken place, the Polythene backing is peeled off.

EXAMPLE 2

According to the procedure described in Example 1, the following ingredients were used to prepare a polymer matrix containing 45.3% by weight of norethisterone:

| | |
|---|---|
| Glycerol | 91.2 mg |
| Compound I | 332.9 mg |
| Ferric chloride | 0.5 mg |
| Norethisterone | 382.8 mg |

EXAMPLE 3

0.4 g of anhydrous p-toluenesulphonic acid was dissolved in 26.2 g of 1,2,6-hexanetriol and 18.4 g of glycerol. The mixture was heated on a steam-bath whilst 44.8 g of 3,4-dyhydro-2H-pyran-2-methyl-(3,4-dihydro-2H-pyran-2-carboxylate) (compound I) were gradually added while stirring over a period of 1.5 hourse. There was formed a clear yellow viscous prepolymer which was heated for a further 20 minutes. The prepolymer was colled and 0.2 g of tert.butylamine was added, followed by 89.6 g of 3,4-dihydro-2H-pyran-2-methyl-(3,4-dihydro-2H-pyran-2-carboxylate. There was thus obtained a light yellow syrup which could be stored for many weeks at room temperature.

5 g of microcrystalline norethisterone were stirred into 5 g of the prepolymer prepared as described in the preceeding paragraph. Following thorough and homogeneous distribution of the norethisterone in the mixture, 0.025 g of anhydrous p-toluenesulphonic acid in 0.225 g of 1,2,6-hexanetriol was rapidly stirred in and the temperature was raised to 100° C. After heating at this temperature for 4 hours, there was obtained a light brown opaque solid comprising norethisterone dispersed in a polymer matrix.

EXAMPLE 4

A solution of 0.021 g of anhydrous ferric chloride in 9.2 g of anhydrous glycerol was heated to 80° C. To this solution were added gradually and while stirring 33.6 g of compound I. This addition was carried out dropwise with no further additions being made until the mixture had become homogeneous. After 0.5 hour, the addition of compound I was complete and there was obtained a light yellow clear liquid.

3% by weight of cortisone were dissolved in the liquid obtained according to the preceding paragraph and the resulting mixture was heated overnight at 80° C. to give a solid, hard, brittle polymer matrix.

EXAMPLE 5

The procedure described in Example 4 was repeated with the exception that 8.4% by weight of spironolactone was incorporated into the polymer matrix. The product obtained was a brittle solid.

EXAMPLE 6

Preparation of a polymer from compounds of formulae II and VI with 1,2,6-hexane triol Both the polydihydropyranyl compounds II and VI can be condensed with triols in the presence of an acid catalyst to yield a crosslinked polymer.

Using a mixture of compounds II and VI containing 25% of II and 1,2,6-hexane triol a stoichiometric polymer was prepared. 2.00 g of 1,2,6-hexane triol containing 0.67% ferric chloride was heated to 80°, and 5.00 g of the said mixture of II and VI was added slowly over half an hour to form a compatible viscous prepolymer, which was then cured at 80° for 20 hours. A glassy yellow polymer with a glass transition temperature of 63° was obtained.

EXAMPLE 7

Preparation of dihydropyran polymer in Example 6 incorporating norethisterone in the matrix 0.8543 g of the stoichiometric prepolymer from a 25.75 parts mixture of II and VI and 1,2,6-hexane triol containing 0.67% ferric chloride as the catalyst was mixed with 0.2136 g norethisterone. The paste with the steroid in suspension was cured over 20 hours at 80°. A hard polymer containing 20% norethisterone was obtained. The glass transition temperature was 53°. Though monomer VI can be used alone its very high viscosity makes the preparation of matrices rather difficult. The addition of 25% of monomer II yields a lower viscosity system much better for the preparation of prepolymers.

EXAMPLE 8

Preparation of the dihydropyran polymer of Example 6 incorporating estradiol in the matrix 1.0995 g of the stoichiometric prepolymer from a 25:75 parts misture of II and VI and 1,2,6-hexane triol containing 0.67% ferric chloride as the catalyst, was mixed with 0.2753 g estradiol to give a composition containing 20% estradiol. The first addition of estradiol dissolved in the prepolymer but further additions remains as a crystalline suspension. The prepolymer paste cured over 20 hours at 80° produced a hard polymer with the steroid partly in solution and partly as a suspension in the matrix. The glass transition temperature was 57°.

EXAMPLE 9

Preparation of a polymer from 3.4-dihydro-2H-pyran-2-yl methyl succinate and 1,2,6-hexane triol.

A stoichiometric formulation of 3 moles of monomer III to 2 moles of 1,2,6-trihydroxyhexane was used. 0.1971 g of 1,2,6-trihydroxyhexane containing 0.67% ferric chloride was heated to 80°. The monomer III was added drop by drop with heating to 80° between additions until the hazy mixture became clear, then further complete addition of the ester when the mixture no longer became hazy when monomer III was added.

After incorporating 0.6904 g of dihydropyran methyl succinate in the triol the prepolymer was returned to the oven at 80° for curing over 20 hours. A polymer slightly soft to a point of pressure and having a Tg of 1° was obtained.

EXAMPLE 10

Preparation of the polymer Example 9 incorporating norethisterone 0.8196 g of the prepolymer exemplified in Example 4 was taken and 0.2049 g norethisterone was added and worked in to form a viscous paste. This cured at 80° over 20 hours to a slightly soft polymer yielding to a point of pressure. The Tg was 4°.

EXAMPLE 11

75 g of 3,4-dihydro-2H-pyran-2-methanol, 57.5 ml of pyridine and 100 ml of benzene were charged into a 1 liter three necked flask fitted with a stirrer, a dropping funnel, and a thermometer. The solution is chilled in an ice-water bath. Phthaloyl chloride 70 g (50 ml) is added from the dropping funnel at such a rate that the reaction temperature is kept at around 40° C. After all the phthaloyl chloride has been added, the mixture is stirred for another hour. 1.25 ml water is then added and the mixture is stirred for another ½ hour. The content is transferred into a suitable container, 50 ml of chloroform and 100 ml of water are added with good stirring. The aqueous layer is removed using a separating funnel. The solution is successively washed with water, dil. HCl, until the solution has no smell of pyridine. 1–2 washings are sufficient then with sodium bicarbonate. The chloroform layer was separated from aqueous layer and the solvent was removed under reduced pressure. The product is a pale yellow semi-solid which has no hydroxyl peak in I.R. spectrum.

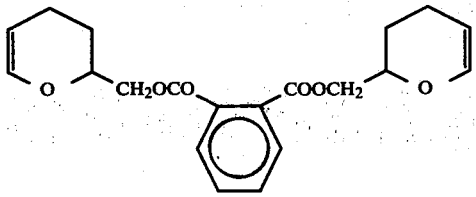

3,4-dihydro-2H-Pyran-2 methylphthalate (Mol wt 358)

| Analysis | Cal % | Found % |
|---|---|---|
| I.R. | C = 67.00<br>H = 6.55<br>double bond —C = C—<br>—C = CH—<br>No hydroxyl bondss (—OH) | C = 66.35<br>H = 6.55<br>(1650 cm$^{-1}$)<br>(3060 cm$^{-1}$) |
| N.M.R. | bonds of unsaturation<br>No hydroxyl | 3.8$_\tau$ |

EXAMPLE 12

Preparation of 3,4-dihydro-2H-Pyran-2-methylsuccinate (Compound III)

This is prepared by a method analogous to that for the preparation of monomer IV. The product is a pale yellow mobile liquid which has no hydroxyl absorption in the infrared but has a strong bond at 1650 cm$^{-1}$.

| Analysis | Cal % | Found % |
|---|---|---|
| I.R. | C = 61.94<br>H = 7.09<br>—C = C—<br>—C = CH<br>—C—O—C<br>No hydroxyl (—OH) | C = 62.03<br>H = 7.29<br>(1650 cm$^{-1}$)<br>(3060 cm$^{-1}$) |
| N.M.R. | Unsaturation<br>No hydroxyl (—OH) | 3.8$_\tau$ |

What we claim is:

1. A biodegradable injection or implantation carrier readily hydrolized by body fluids and thereby gradually releasing a steroid on administration of the compound, comprising a steroid compound entrapped within at least about an equal weight of a polymeric matrix composed of a cross-linked copolymer of stoichiometric amounts of each of a compound containing two or more groups selected from the group glycerol, sorbitol, erythritol, inositol, glycols based on polyethylene oxide, 4,4'-dihydroxyphenyl-2,2-propane, 1,2—dihydroxybenzene, 1,3-dihydroxy-benzene, 1,4-dihydroxybenzene, 1,2,3-trihydroxy-benzene, 1,2,4-trihydroxybenzene, 1,3,5—trihydroxy-benzene, lactic acid, malic acid, 2-hydroxy-isobutyric acid, 10-hydroxydecanoic acid, 12-hydroxyoctadecanoic acid, 12-hydroxy(cis)-9-octadecenoic acid, 2-hydroxycyclo-hexanecarboxylic acid (hexahydrosalicyclic acid), 2-hydroxy-2—phenyl-(D)-propionic acid, diphenylhydroxyacetic acid, ascorbic acid, citric acid, tartaric acid, 2-hydroxy-3-methyl-(D)—succinic acid, 2-hydroxybenzoic acid, 3-hydroxybenzoic acid, 4-hydroxybenzoic acid, 2,3-dihydroxybenzoic acid, 2,4-dihydroxybenzoic acid, 2,5-dihydroxybenzoic acid, 2,6-dihydroxybenzoic acid, 2,3,4-trihydroxybenzoic acid, 2,4,5-trihydroxybenzoic acid, 2,4,6-trihydroxybenzoic acid, 3,4,5-trihydroxybenzoic acid, oxalic acid, malonic acid, succinic acid, glutaric acid, adipic acid, 1,2-cyclohexanedicarboxylic acid, 1,3-cyclohexane-dicarboxylic acid, 1,4-cyclohexanedicarboxylic acid, phthalic acid, isophthalic acid, teraphthalic acid, and mixtures thereof, consisting of —OH and —COOH groups and a bisdihydropyran of general formula I.

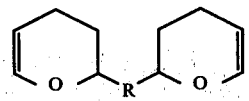

I wherein R is an organic bridging group which is unreactive to the —OH or —COOH groups selected from the group consisting of:

II

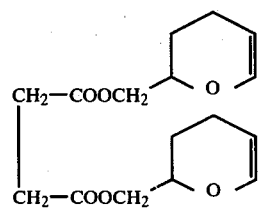

III

-continued

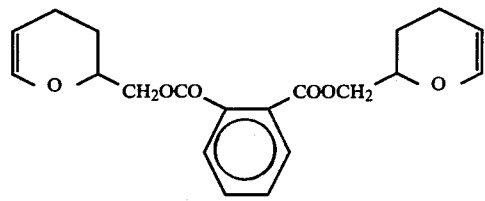
IV

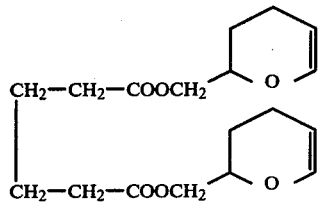
V

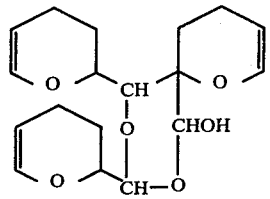
VI

2. A medicinal composition according to claim 1 wherein said compound is glycerol, sorbitol, erythritol, inositol a hydroxy fatty acid or a glycol based on polyethylene oxide.

3. A medicinal composition according to claim 1, wherein the steroidal material is selected from norethisterone and norethisterone acetate.

4. A medicinal composition according to claim 1, wherein the ratio of steroidal material to copolymer is from about 50:50 by weight to about 60:40 by weight.

5. A medicinal composition according to claim 1, which is modified by the incorporation therein of a substance selected from an inert pharmaceutically acceptable solvent and an inert pharmaceutically acceptable oil.

6. A medicinal composition according to claim 1, in the form of a dispersion in a pharmaceutically acceptable liquid carrier adapted for subcutaneous or intramuscular administration.

7. A medicinal composition according to claim 1, in the form of an implant adapted for subcutaneous administration.

* * * * *